United States Patent [19]

Robbins

[11] Patent Number: 4,551,544
[45] Date of Patent: Nov. 5, 1985

[54] TITANIUM ESTER COMPOSITIONS HAVING DEPRESSED FREEZING POINTS

[75] Inventor: Gordon B. Robbins, Edison, Nebr.

[73] Assignee: E. I. Du Pont de Nemours and Company, Wilmington, Del.

[21] Appl. No.: 642,813

[22] Filed: Aug. 21, 1984

Related U.S. Application Data

[63] Continuation of Ser. No. 439,567, Nov. 5, 1982, abandoned.

[51] Int. Cl.$^4$ ................................................. C07F 7/28
[52] U.S. Cl. ....................................................... 556/40
[58] Field of Search ...................................... 260/429.5

[56] References Cited

U.S. PATENT DOCUMENTS 2,680,108 6/1954 Schmidt ........................... 260/429.5
4,313,851 2/1982 Barfurth et al. ............. 260/429 R X

OTHER PUBLICATIONS

J. Oil and Colour Chem. Assoc., 31, 405 (1948).

Yamamoto et al., J.A.C.S., 79, 4344–4348 (1957).

Primary Examiner—Helen M. S. Sneed

[57] ABSTRACT

The reaction product obtained by combining (i) a titanate $(R^1O)_4Ti$ (particularly tetraisopropyl titanate) with (ii) 2,4-pentanedione and (iii) a substance which is either (a) at least one other titanate $(R^2O)_4Ti$ (particularly tetramethyl or tetra-n-butyl titanate or mixtures thereof) or (b) at least one alcohol $R^3OH$ (particularly methanol or n-butanol or mixtures thereof)

wherein $R^2$ and $R^3$ differ from $R^1$ and are each methyl, ethyl, 2-chloroethyl, isopropyl, n-propyl, n-butyl, n-pentyl, 2-pentyl, 3-methylbutyl, 2-methoxyethyl, or methoxyethoxyethyl and the titanate:pentanedione mol ratio is in the range between 1:1 and 1:2. The quantity of said substance is sufficient, even in the presence of a nucleating agent, to depress the freezing point of the reaction product obtained by combining said first-mentioned titanate with 2,4-pentanedione. Also methods of preparing the reaction product are disclosed.

18 Claims, 1 Drawing Figure

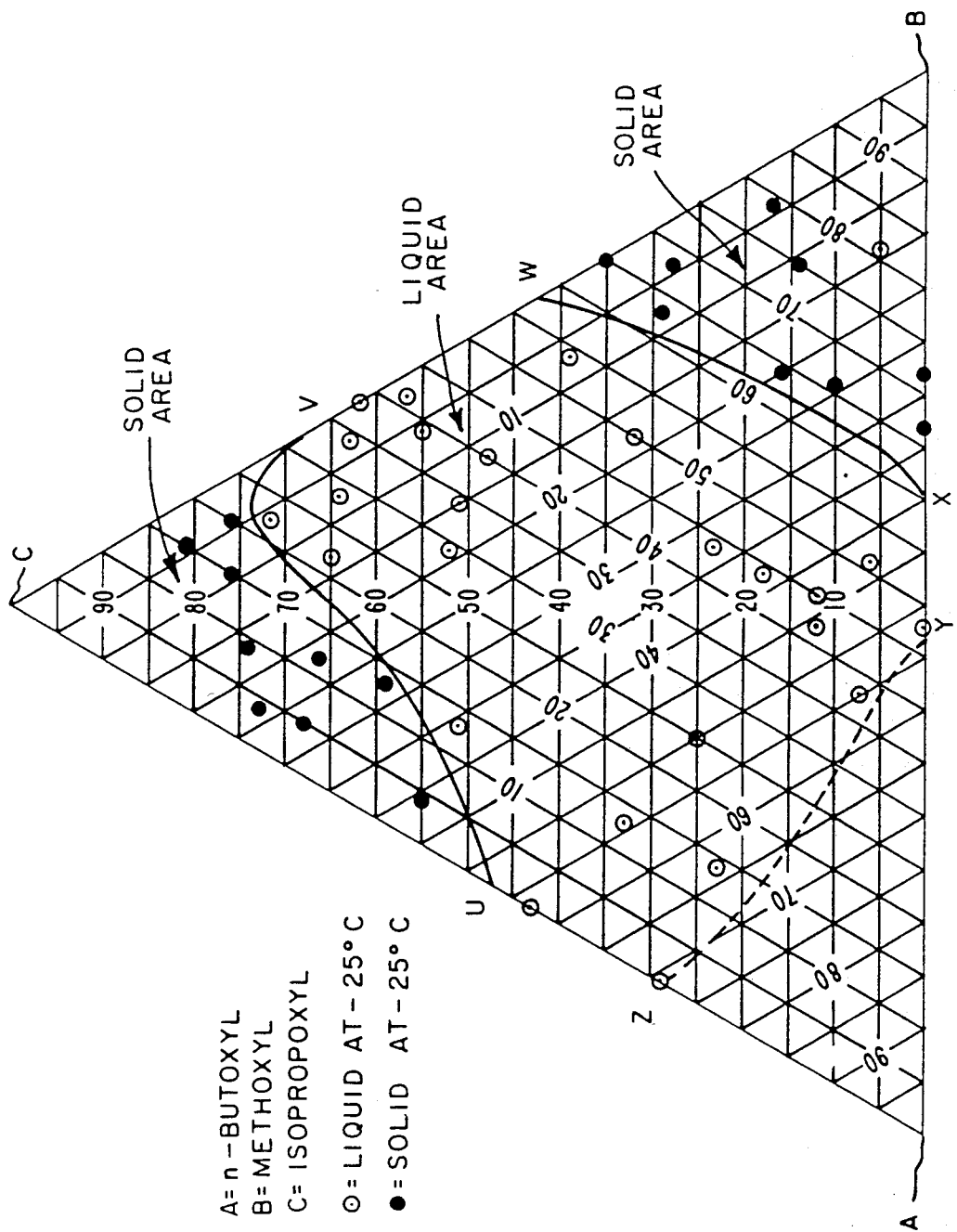

TITANIUM ESTER COMPOSITIONS HAVING DEPRESSED FREEZING POINTS

CROSS REFERENCE TO RELATED APPLICATION

This application is a continuation of application Ser. No. 439,567 filed Nov. 5, 1982, now abandoned.

BACKGROUND OF THE INVENTION

The present invention relates to a reaction product of a titanium ester and 2,4-pentanedione which has been modified so as to lower its freezing point.

It has long been known that titanium esters react with high molecular weight hydroxyl-containing compounds so as to cross-link them and produce gels; J. Oil and Colour Chem Assoc. 31, 405 (1948). However, the cross-linking reaction made through the use of simple alkyl esters of titanium proceeds too rapidly for most industrial uses. The cross-linking rate imparted by titanium esters can be depressed by combining a titanium ester with a variety of multifunctional compounds including 2,4-pentanedione (also known as acetylacetone); U.S. Pat. No. 2,680,108. It should be noted that there is disagreement as to the structure of the complexes or chelates so-formed; cf. the structure given in the patent with that given by Yamamoto et al., J.A.C.S. 79 (1957), 4344-8.

The reaction product of tetraisopropyl titanate (also known as tetraisopropoxytitanium) and 2,4-pentanedione, at a titanate:pentanedione mol ratio of 1:2, finds several industrial uses. Among others, that reaction product is used to cross-link high molecular weight compounds (e.g., hydroxypropyl guar gum), and the cross-linked high molecular material is used to fracture oil-bearing formations. That reaction product is normally a liquid, and sometimes it remains in the liquid state even after having been supercooled to some considerable extent. However, in the supercooled state, it sometimes spontaneously freezes, especially in the presence of a nucleating agent, such as dust or a part of the reaction product in crystal form. The reaction product of tetraisopropyl titanate and 2,4-pentanedione at a 1:1 mol ratio has an even greater tendency to freeze.

In U.S. Pat. No. 4,313,851, it is proposed that the addition of a small amount of water will inhibit crystallization of the reaction product of one mol of tetraisopropyl titanate with two mols of 2,4-pentanedione. The technique used in that patent results in hydrolysis of that reaction product, liberating isopropyl alcohol. In any event, that technique did not prevent freezing in the presence of a nucleating agent.

SUMMARY OF THE INVENTION

The present invention provides a titanium composition, the freezing point of which has been depressed without adversely affecting its utility in cross-linking high molecular weight compounds. The present invention also provides processes by which to prepare the compositions of the present invention. The composition of the present invention comprises the reaction product of a titanium ester with 2,4-pentanedione and either at least one other titanium ester or at least one alcohol which provides an alkoxy radical differing from that present in the original titanium ester.

DETAILED DESCRIPTION OF THE INVENTION

In particular, the composition of the present invention comprises the reaction product obtained by combining (i) a titanate represented by the empirical formula

$(R^1O)_4Ti$ with (ii) 2,4-pentanedione and (iii) a substance which is either (a) at least one other titanate represented by the empirical formula

$(R^2O)_4Ti$ or (b) at least one alcohol represented by the empirical formula

$R^3OH$ wherein
the titanate:pentanedione mol ratio is in the range between 1:1 and 1:2;
$R^2$ and $R^3$ differ from $R^1$; and
$R^1$, $R^2$ and $R^3$ are each methyl, ethyl, 2-chloroethyl, isopropyl, n-propyl, n-butyl, n-pentyl, 2-pentyl, 3-methylbutyl, 2-methoxyethyl, or methoxyethoxyethyl.

The quantity of substance (a) or (b) is sufficient, even in the presence of a nucleating agent, to depress the freezing point of the reaction product obtained by combining the first-mentioned titanate with 2,4-pentanedione.

The preferred reaction product is that obtained by combining a tetraalkyl titanate with 2,4-pentanedione, at a titanate:pentanedione mol ratio between 1:1 and 1:2, and one or more alcohols. In one such embodiment, tetraisopropyl titanate is reacted with 2,4-pentanedione, at a mol ratio between 1:1 and 1:2; all or part of the isopropanol thereby generated is removed by distillation, and one or more of the $R^3OH$ alcohols other than isopropanol is added to the reaction product. The concentration of titanium in the final product is preferably substantially the same as in the reaction product of the first-mentioned titanium ester and 2,4-pentanedione.

In a more preferred embodiment, tetraisopropyl titanate is reacted with 2,4-pentanedione, at a titanate:pentanedione mol ratio of 1:2; all or part of the isopropanol thereby generated is removed by distillation and a mixture of methanol and n-butanol is added in a quantity sufficient on a molar basis to replace the isopropanol which has been removed. The reaction products thereby obtained contain methoxy, isopropoxy and n-butoxy substituents in the proportions, in mol percentages, shown for the liquid products identified in the FIGURE; i.e., the area UVWXYZ (Yamamoto et al., supra, report tetra-n-butyl titanate to be noncrystalline). The most preferred composition is that which contains about 51 mol % isopropoxy, about 15 mol % n-butoxy and about 34 mol % methoxy (Example 1). In similar embodiments, one can substitute other titanates for tetraisopropyl titanate, e.g., tetramethyl titanate (sometimes called titanium methoxide), tetra-n-butyl titanate, or the like, and alcohols other than methanol or n-butanol respectively.

The reaction of (R¹O)Ti and one or more (R²O)₄Ti with 2,4-pentanedione is exothermic. The reaction can be run at a temperature between room temperature and reflux temperature; i.e., about 20°–85° C. If one wishes to conduct the reaction at the lower end of that temperature range, one may do it either by providing a cooling means or by adding the titanate to the pentanedione at a slow enough rate that the temperature remains in the lower portion of the range, e.g., 20°–50° C. R¹OH, liberated in that reaction, is removed. When that reaction product is to be reacted with one or more R³OH, usually the amount of R¹OH that is removed is substantially the same on a molar basis as the amount of R³OH being used. Most often the R¹OH will be removed before adding R³OH. However, it is not always necessary to do so; e.g., one can remove R¹OH by distillation if the boiling point of R³OH is sufficiently higher than that of R¹OH.

In attempting to modify the reaction product of the titanate and pentanedione so as to lower its freezing point, one is hampered by the tendency of such compositions to supercool for long periods of time without showing any tendency to freeze. Only by exposing the modified reaction product to lower temperature in the presence of seed crystals can one be certain that the freezing point of the modified reaction product has truly been reduced significantly.

In the examples that follow the compositions of the invention are characterized as to mol percentage alkoxy content and temperature characteristics. The former is obtained by calculating the mol percentage of each individual alkoxy radical in the sum of the mols of alkoxy radicals provided by (R¹O)₄Ti and (R²O)₄Ti or by (R¹O)₄Ti and R³OH. The latter is determined by holding the compositions at about −25° C. for at least 4 hours, and usually overnight (about 16 hours), and thereafter seeding an aliquot of the composition with crystals of the reaction product of (R¹O)₄Ti and 2,4-pentanedione, and sometimes additionally with crystals of the reaction product of (R²O)₄Ti and 2,4-pentanedione. Thereafter, the compositions are inspected periodically to determine whether the composition has frozen, and if so, how long after seeding it occurred. If a composition freezes at −25° C., it is then observed at +2° C. and, if necessary, at room temperature (20°–25° C.) to determine if and when it becomes liquid.

EXAMPLE 1

(A) A flask, vented through a reflux condenser and a bubble trap, was provided with a nitrogen atmosphere so as to exclude atmospheric moisture. To the flask were added 802 g of 2,4-pentanedione (about 8 mols). Taking care so as to give minimal exposure to atmospheric moisture, 1136 g of tetraisopropyl titanate (about 4 mols) were transferred to a dropping funnel having a pressure equalizing tube, and from that dropping funnel with stirring to the flask. The titanate was added slowly to the 2,4-pentanedione so as to maintain the temperature in the range between 20° and 50° C. After stirring for one hour, the reaction product was transferred to a single neck flask and isopropanol was removed by distillation to a final condition of 40° C. and 40 mm Hg so as to give a final weight of 1460 g (had all of the isopropanol been removed, a product weighing about 1458 g would have been obtained). A 200 g quantity each of methanol (about 6.25 mols) and n-butanol (about 2.7 mols) were added to the distilled product along with 72 g of isopropanol (about 1.2 mols) to give a composition having a density of 1.015 at 20° C. Of the total alkoxy substituents in that composition, about 34 mol percent were methoxy; about 51 mol percent were isopropoxy and about 15 mol percent were n-butoxy. When seeded and tested as described above at −25° C., no freezing was evident, even after 21 days. The temperature characteristics of the composition of this Example 1(A) are also illustrated in the FIGURE.

(B) The procedure of this Example was repeated, except that 4 g of water (about 0.22 mol) were mixed with the 2,4-pentanedione prior to addition of the tetraisopropyl titanate. When seeded and tested as described above at −25° C., no freezing was evident even after 21 days.

EXAMPLE 2

Compositions were prepared by the technique of Example 1(A), with the following modifications. Upon distilling to a final condition of 40° C. and 40 mm Hg, the weight of the resulting composition was 1460 g. That composition was divided into aliquots of 91.2 g containing 0.25 mol of titanium. To one aliquot was added 30 g of isopropanol so as to provide a control. All other aliquots were made up to 121.2 g by the addition of various alcohols (each aliquot was made up to 9.9 weight percent titanium, the titanium content of Du Pont's Tyzor® AA reaction product of one mol of tetraisopropyl titanate and 2 mols of 2,4-pentanedione). The aliquots were cooled to about −25° C. and seeded with solid particles of the reaction product of one mol of tetraisopropyl titanate and 2,4-pentanedione (1:2 titanate:pentanedione mol ratio). Aliquots having a methoxy content were additionally seeded with solid particles of the reaction product of tetramethyl titanate and 2,4-pentanedione (1:2 mol ratio). After being exposed at −25° C. for about ten days, samples were examined. Solid samples were thereafter exposed to +2° C. for several days and then at room temperature (20°–25° C.). Table I sets forth the composition of the aliquots in terms of their mol percentage alkoxy content and describes their condition at various temperatures.

TABLE I

| Example (Aliquot) | Alkoxy Content | Temperature Characteristics | | |
|---|---|---|---|---|
| | | −25° C. | +2° C. | Room Temperature |
| 2(A) | 35% Isopropoxy-65% Methoxy | Solid | Solid | 95 Vol. % Fluid |
| 2(B) | 62% Isopropoxy-38% Methoxy | Fluid | — | — |
| 2(C) | 43% Isopropoxy-57% Ethoxy | Fluid | — | — |
| 2(D) | 70% Isopropoxy-30% Ethoxy | 60 Vol. % Solid | 95 Vol. % Fluid | Fluid |
| 2(E) | 50% Isopropoxy-50% n-Propoxy | Solid | 95 Vol. % Fluid | Fluid |
| 2(F) | 55% Isopropoxy-45% n-Butoxy | Solid | Fluid | — |
| 2(G) | 79% Isopropoxy-21% n-Butoxy | Solid | Fluid | — |
| 2(H) | 43% Isopropoxy-17% n-Butoxy- | Fluid | — | — |

TABLE I-continued

| Example (Aliquot) | Alkoxy Content | Temperature Characteristics | | |
|---|---|---|---|---|
| | | −25° C. | +2° C. | Room Temperature |
| | 40% Methoxy | | | |
| 2(I) | 69% Isopropoxy-9% n-Butoxy-22% Methoxy | Fluid | — | — |
| 2(J) | 74% Isopropoxy-10% n-Butoxy-16% Ethoxy | Solid | Fluid | — |
| Control | 100% Isopropoxy | Solid | 90 Vol. % Solid | Fluid |

EXAMPLE 3

The procedure of Example 2 was repeated except that one cc of water (about 0.06 mol) per mol of titanium was added to the 2,4-pentandione before the titanate was added to it. The mol percentage alkoxy content and the temperature characteristics of the resulting compositions is given in Table II.

TABLE II

| Example (Aliquot) | Alkoxy Content | Temperature Characteristics | | |
|---|---|---|---|---|
| | | −25° C. | +2° C. | Room Temperature |
| 3(A) | 35% Isopropoxy-65% Methoxy | Solid | Solid | Fluid |
| 3(B) | 62% Isopropoxy-38% Methoxy | Solid | Fluid | — |
| 3(C) | 43% Isopropoxy-57% Ethoxy | Fluid | — | — |
| 3(D) | 70% Isopropoxy-30% Ethoxy | 65 Vol. % Fluid | Fluid | — |
| 3(E) | 50% Isopropoxy-50% n-Propoxy | Solid | Fluid | — |
| 3(F) | 75% Isopropoxy-25% n-Propoxy | Solid | Fluid | — |
| 3(G) | 55% Isopropoxy-45% n-Butoxy | 75 Vol. % Solid | Fluid | — |
| 3(H) | 79% Isopropoxy-21% 21% n-Butoxy | Solid | Fluid | — |
| 3(I) | 59% Isopropoxy-41% n-Pentoxy | Fluid | — | — |
| 3(J) | 81% Isopropoxy-19% n-Pentoxy | Solid | Fluid | — |
| 3(K) | 50% Isopropoxy-41% 2-Pentoxy | Fluid | — | — |
| 3(L) | 81% Isopropoxy-19% 2-Pentoxy | Solid | Fluid | — |
| 3(M) | 59% Isopropoxy-41% 3-Methylbutoxy | Fluid | — | — |
| 3(N) | 81% Isopropoxy-19% 3-Methylbutoxy | Solid | Fluid | — |
| 3(O) | 49% Isopropoxy-19% n-Butoxy-32% Ethoxy | Fluid | — | — |
| 3(P) | 53% Isopropoxy-21% n-Butoxy-26% n-Propoxy | Solid | Fluid | — |
| 3(Q) | 45% Isopropoxy-12% n-Butoxy-43% Methoxy | Fluid | — | — |
| 3(R) | 59% Isopropoxy-20% 2-Pentoxy-21% 3-Methylbutoxy | Fluid | — | — |
| 3(S) | 57% Isopropoxy-43% 2-Chloroethoxy | Fluid | — | — |
| 3(T) | 80% Isopropoxy-20% 2-Chloroethoxy | 75 Vol. % Fluid | Fluid | — |
| 3(U) | 59% Isopropoxy-41% 2-Methoxyethoxy | 75 Vol. % Fluid | Fluid | — |
| 3(V) | 79% Isopropoxy-21% 2-Methoxyethoxy | Solid | Fluid | — |
| 3(W) | 67% Isopropoxy-33% Methoxyethoxy-ethoxy | Fluid | — | — |
| 3(X) | 86% Isopropoxy-14% Methoxyethoxy-ethoxy | Solid | 80 Vol. % Solid | Fluid |
| Control | 100% Isopropoxy | Solid | Solid | Fluid |

EXAMPLE 4

Example 3 was repeated with 401 g of 2,4-pentanedione (about 4 mols), 2 g of water (about 0.11 mol) and 568 g of tetraisopropyl titanate (about 2 mols). The resulting reaction product was distilled to a final condition of 40° C. and 40 mm Hg and a weight of 736 g, and divided into 8 aliquots to which varying amounts of methanol, isopropanol and n-butanol were added to give the compositions set forth in Table III and the temperature characteristics set forth in the FIGURE.

EXAMPLE 5

Example 4 was repeated except that distillation was continued to a weight of 728 g. The composition of the 8 aliquots is shown in Table III and their temperature characteristics are shown in the FIGURE.

EXAMPLE 6

Example 3 was repeated with 100.3 g of 2,4-pentanedione (about 1 mol), 0.5 cc of water (about 0.03 mol) and 142 g of tetraisopropyl titanate (about 0.5 mol), stirred ½ hour and distilled to 182.8 g. The composition was divided into 3 aliquots to which alcohols were added to give the composition shown in Table III. The temperature characteristics of those aliquots is shown in the FIGURE.

EXAMPLE 7

Example 6 was repeated except that distillation was discontinued when a composition weighing 193.4 g was obtained. The composition of the 3 aliquots is shown in Table III and their temperature characteristics are shown in the FIGURE.

EXAMPLE 8

The technique of the preceding examples was repeated. However, 200.5 g of 2,4-pentanedione (about 2 mols) and 1 g of water (about 0.06 mol) were mixed and swept with nitrogen. Then 172 g of tetramethyl titanate (about 1 mol) were added and the reaction product was and stirred until essentially clear, filtered and subjected to vacuum until a weight of 301.5 g was obtained. The resulting composition was divided into 16 aliquots, to 11 of which various alcohols were added so as to give the compositions shown in Table III which have the temperature characteristics shown by the FIGURE.

EXAMPLE 9

Example 8 was repeated. However, 70.2 g of 2,4-pentanedione (about 0.7 mol), 0.35 cc of water (about 0.02 mol) and 60.2 g of tetramethyl titanate (about 0.35 mol) were used. The composition was stirred until essentially clear, filtered and 50 cc of methanol were added. The resulting composition was distilled to 107 g and the 5 aliquots which were prepared but not used in Example 8 were added to give a total weight of 201.2 g. Four aliquots, each weighing 19.25 g, were taken from that final composition and various alcohols added so as to give the compositions shown in Table III which have the temperature characteristics shown in the FIGURE.

EXAMPLE 10

The procedure of the preceding examples was repeated using 200.5 g of 2,4-pentanedione (about 2 mols), 1 cc of water (about 0.06 mol) and 340 g of tetrabutyl titanate (about 1 mol). The composition was stirred for 1 hour, distilled to a weight of 392 g and divided into 16 aliquots, to 8 of which varying amounts of various alcohols were added so as to give the compositions shown by Table III, the temperature characteristics for which are shown in the FIGURE.

TABLE III

| Example | Mol Percent | | |
|---|---|---|---|
| (Aliquot) | Methoxy | Isopropoxy | n-Butoxy |
| 4(A) | 40 | 48 | 12 |
| 4(B) | 28 | 64 | 8 |
| 4(C) | 22 | 65 | 13 |
| 4(D) | 15 | 76 | 9 |
| 4(E) | 22 | 72 | 6 |
| 4(F) | 39 | 55 | 6 |
| 4(G) | 29 | 52 | 19 |
| 4(H) | 15 | 81 | 4 |
| 5(A) | 12 | 66 | 22 |
| 5(B) | 13 | 51 | 36 |
| 5(C) | 4 | 55 | 41 |
| 5(D) | 13 | 59 | 28 |
| 5(E) | 20 | 76 | 4 |

TABLE III-continued

| Example | Mol Percent | | |
|---|---|---|---|
| (Aliquot) | Methoxy | Isopropoxy | n-Butoxy |
| 5(F) | 34 | 63 | 3 |
| 5(G) | 41 | 57 | 2 |
| 5(H) | 52 | 48 | — |
| 6(A) | 5 | 63 | 32 |
| 6(B) | 59 | 37 | 4 |
| 6(C) | 54 | 39 | 7 |
| 7(A) | 5 | 68 | 27 |
| 7(B) | 4 | 73 | 23 |
| 7(C) | 9 | 74 | 17 |
| 8(A) | 48 | — | 52 |
| 8(B) | 72 | — | 28 |
| 8(C) | 67 | — | 33 |
| 8(D) | 64 | 16 | 20 |
| 8(E) | 63 | 29 | 8 |
| 8(F) | 75 | 14 | 11 |
| 8(G) | 66 | 10 | 24 |
| 8(H) | 44 | 18 | 38 |
| 8(I) | 44 | 23 | 33 |
| 8(J) | 45 | 12 | 43 |
| 8(K) | 50 | 32 | 18 |
| 9(A) | 87 | 8 | 7 |
| 9(B)* | 81 | 5 | 14 |
| 9(C) | 79 | 17 | 4 |
| 9(D) | 68 | 28 | 4 |
| 10(A) | — | 43 | 57 |
| 10(B) | — | 29 | 71 |
| 10(C) | 25 | 25 | 50 |
| 10(D) | 13 | 33 | 54 |
| 10(E) | 51 | 6 | 43 |
| 10(F) | 42 | 12 | 46 |
| 10(G) | 38 | 7 | 55 |
| 10(H) | 14 | 23 | 63 |

*Note:
The Figure shows that this composition did not freeze at −25° C., whereas other compositions containing 63 to 79 mol % methoxy substituents were solid at −25° C. Apparently, seeding did not overcome supercooling in Example 9(B).

EXAMPLE 11

In accordance with the technique described for the preceding examples, 568 g of tetraisopropyl titanate (about 2 mols) were combined with 200 g of 2,4-pentanedione (about 2 mols) and distilled to a weight of 708 g. The resulting composition was divided into 8 aliquots and diluted with various alcohols to 121.5 g. The percentage alkoxy content in each of the aliquots and their temperature characteristics are shown in Table IV.

TABLE IV

| Example | | Temperature Characteristics | | |
|---|---|---|---|---|
| (Aliquot) | Alkoxy Content | −25° C. | +2° C. | Room Temperature |
| 11(A) | 42% Isopropoxy-58% Methoxy | Fluid | — | — |
| 11(B) | 51% Isopropoxy-49% Ethoxy | Solid | Solid | 50 Vol. % Fluid |
| 11(C) | 58% Isopropoxy-42% n-Propoxy | Solid | Solid | 90 Vol. % Solid |
| 11(D) | 63% Isopropoxy-37% n-Butoxy | 90 Vol. % Fluid | 95 Vol. % Fluid | Fluid |
| 11(E) | 67% Isopropoxy-33% n-Pentoxy | Solid | Solid | 85 Vol. % Fluid |
| 11(F) | 50% Isopropoxy-35% Methoxy-15% n-Butoxy | Fluid | — | — |
| 11(G) | 63% Isopropoxy-29% Methoxy-8% n-Butoxy | Fluid | — | — |
| 11(H) | 80% Isopropoxy-11% Methoxy-9% n-Butoxy | 97 Vol. % Fluid | Trace Solid | Fluid |
| Control | 100% Isopropoxy | Solid | Solid | 85 Vol. % Fluid |

EXAMPLE 12

With minimum exposure to atmospheric moisture, 17.2 g of tetramethyl titanate (about 0.1 mol), 34.0 g of tetra-n-butyl titanate (about 0.1 mol) and 28.4 g of tetraisopropyl titanate (about 0.1 mol) were mixed in a flask provided with an agitator, thermometer and nitrogen inlet. Thereafter, 60 g of 2,4-pentanedione (about 0.6 mol) were added, stirred for 1 hour at 40°–50° C. and filtered to remove a faint haze. The resulting composition contained 33⅓ mol percent of each of methoxy, isopropoxy and n-butoxy substituents.

EXAMPLE 13

Example 12 was repeated with 25.8 g of tetramethyl titanate (about 0.15 mol), 51 g of tetra-n-butyl titanate (about 0.15 mol) and 60 g of 2,4-pentanedione (about 0.6 mol) to give a composition containing 50 mol percent of each of methoxy and n-butoxy substituents.

A control for the compositions of Examples 12 and 13 was prepared by reacting 200 g of 2,4-pentanedione (about 2 mols) with 284 g of tetraisopropyl titanate (about 1 mol).

Aliquots of the composition of Examples 12 and 13 and of the control for them were seeded with crystals of the reaction product of 2,4-pentanedione and tetraisopropyl titanate (2:1 mol ratio). The aliquot of the composition of Example 12 was also seeded with the reaction product of 2,4-pentanedione and tetramethyl titanate (2:1 mol ratio). The compositions of Examples 12 and 13 gave no crystallization after 2 weeks at −25° C. That of the control crystallized within 3 hours after seeding.

EXAMPLE 14

To 142 g (about 0.5 mol) of tetraisopropyl titanate were added 100 g (about 1 mol) of 2,4-pentanedione and 120 g (about 1 mol) of methylcarbitol (the monomethyl ether of diethylene glycol). The composition was distilled to a final condition of 50° C. and 10 mm Hg to give a final weight of 248 g.

EXAMPLE 15

The procedure of Example 14 was repeated; however, 240 g (about 2 mols) of methylcarbitol were used and distillation provided a final weight of 367 g.

EXAMPLE 16

The procedure of Example 14 was repeated; however, 60 g (about 0.6 mol) of 2,4-pentanedione were used and 40 g (about 0.33 mol) of methylcarbitol to give a final weight of 242 g.

EXAMPLE 17

Example 16 was repeated; however, 100 g (about 0.83 mol) of methylcarbitol were used and distillation was continued to a final weight of 216 g.

To serve as a control for Examples 14–17, Example 14 was repeated; however, no methylcarbitol was used.

Aliquots of the compositions of Examples 14–17 and of the control were seeded at −25° C. with crystals of the reaction product of 1 mol of tetraisopropyl titanate and 2 mols of 2,4-pentanedione. When the aliquots were checked 2 days later, the control was frozen solid; there was no evidence of crystals in the compositions of Examples 14, 15 and 17, while the composition of Example 16 was about 90 volume percent liquid. When those same aliquots were again checked 6 days later, substantially no change had taken place.

EXAMPLE 18

To 200 g of 2,4-pentanedione (about 2 mols) were added 3 g of water (about 0.17 mol). The mixture was swept with nitrogen and 284 g of tetraisopropyl titanate (about 1 mol) were added at a temperature between 20° and 30° C. The reaction product was distilled under vacuum to 40° C. and a weight of 355 g. With agitation at 40°–50° C., 132 g of ethanol (about 2.87 mols) were added with agitation at 40°–50° C. The alkoxy content of the resulting product was about 39 mol % isopropoxy and about 61 mol % ethoxy. When tested at −25° C. by the technique described above, there was no freezing even after 21 days.

Example 18 was duplicated to give the same composition having substantially the same characteristics at −25° C. It will be noted that those results are consistent with those of Example 3(C). However, it should be noted that for some unexplained reason, the first time the technique of the Example was run, the aliquot froze at −25° C.

EXAMPLE 19

Example 18 was repeated, except that the weight of product after vacuum distillation was 355.5 g, and 131.5 g of methanol (about 4.1 mols) were added thereto (rather than ethanol). The alkoxy content of the resulting product was about 35 mol % isopropoxy and about 65 mol % methoxy. When an aliquot of the resulting product was seeded with crystals of both tetraisopropyl titanate and tetramethyl titanate and stored at −25° C., there was no freezing, even after 21 days of such exposure.

It will be noted that results of low temperature exposure according to this Example 19 are different from those of Examples 2(A) and 3(A) given in Tables I and II. However, it will be observed that the amount of water added according to this Example is about 0.17 mol per mol of tetraisopropyl titanate while that of Example 3(A) is about 0.06 mol and no water was added in Example 2(A).

Attempt to Use Water to Inhibit Crystallization

As in the foregoing examples, 200 g of 2,4-pentanedione (about 2 mols), 1.8 g of water (about 0.1 mol) and 284 g of tetraisopropyl titanate (about 1 mol) were combined and refluxed for 1 hour. On cooling the composition weighed 483.9 g, it was chilled to −25° C. and seeded with crystals of the reaction product of tetraisopropyl titanate and 2,4-pentanedione (mol ratio of 1:2). Within 18 hours at −25° C., it had frozen solid.

I claim:

1. A composition comprising the reaction product obtained by reacting (i) a titanate represented by the empirical formula (R¹O)₄Ti with (ii) 2,4-pentanedione and removing all or part of the R¹OH thereby generated and replacing all or part of it by combining the resulting titanate/pentanedione reaction product with (iii) a substance which is either
   (a) at least one other titanate represented by the empirical formula (R²O)₄Ti or
   (b) at least one alcohol represented by the empirical formula

R³OH wherein
the titanate:pentanedione mol ratio is in the range between 1:1 and 1:2;
$R^2$ and $R^3$ differ from $R^1$; and
$R^1$, $R^2$ and $R^3$ are each methyl, ethyl, 2-chloroethyl, isopropyl, n-propyl, n-butyl, n-pentyl, 2-pentyl, 3-methylbutyl, 2-methoxyethyl, or methoxyethoxyethyl;
the quantity of said substance being sufficient, even in the presence of a nucleating agent, to depress the freezing point of the reaction product obtained by combining said first-mentioned titanate with 2,4-pentanedione.

2. The composition of claim 1 wherein said substance is at least one alcohol represented by the empirical formula $$R^3OH.$$

3. The composition of claim 1 wherein the titanate represented by the empirical formula $$(R^1O)_4Ti$$

is tetraisopropyl titanate.

4. The composition of claim 3 wherein said substance is at least one alcohol represented by the empirical formula $$R^3OH.$$

5. The composition of claim 4 wherein said substance comprises methanol.

6. The composition of claim 4 wherein said substance comprises ethanol.

7. The composition of claim 4 wherein said substance comprises n-butanol.

8. The composition of claim 4 wherein said substance comprises a mixture of methanol and n-butanol.

9. The composition of claim 4 containing methoxy, isopropoxy and n-butoxy substituents in the molar proportions defined by the area UVWXYZ in the FIGURE.

10. The composition of claim 9 which contains about 51 mol % isopropoxy, about 15 mol % n-butoxy and about 34 mol % methoxy substituents.

11. The composition of claim 1 in which the $(R^1O)_4Ti$:2,4-pentanedione mol ratio is 1:2.

12. A process for depressing the freezing point of a titanate/2,4-pentanedione reaction product which comprises reacting (i) a titanate represented by the empirical formula $$(R^1O)_4Ti$$

with (ii) 2,4-pentanedione and removing all or part of the $R^1OH$ thereby generated and replacing all or part of it by combining the resulting titanate/pentanedione reaction product with (iii) a substance which is either
(a) at least one other titanate represented by the empirical formula $$(R^2O)_4Ti$$

or
(b) at least one alcohol represented by the empirical formula $$R^3OH$$

wherein
the titanate:pentanedione mol ratio is in the range between 1:1 and 1:2;
$R^2$ and $R^3$ differ from $R^1$; and
$R^1$, $R^2$ and $R^3$ are each methyl, ethyl, 2-chloroethyl, isopropyl, n-propyl, n-butyl, n-pentyl, 2-pentyl, 3-methylbutyl, 2-methoxyethyl, or methoxyethoxyethyl;
the quantity of said substance being sufficient, even in the presence of a nucleating agent, to depress the freezing point of the reaction product obtained by combining said first-mentioned titanate with 2,4-pentanedione.

13. The process of claim 12 wherein said substance is at least one alcohol represented by the empirical formula $$R^3OH.$$

14. The process of claim 12 in which said titanate represented by the empirical formula $$(R^1O)_4Ti$$

is tetraisopropyl titanate.

15. The process of claim 14 wherein tetraisopropyl titanate is reacted with 2,4-pentanedione, all or part of the isopropanol thereby generated is removed from the reaction product and one or more of the alcohols represented by the empirical formula $$R^3OH$$

is added to the reaction product

16. The process of claim 15 wherein the titanate:pentanedione mol ratio is 1:2, all or part of the isopropanol is removed by distillation and a mixture of methanol and n-butanol is added in a quantity sufficient to replace the isopropanol which has been removed.

17. The process of claim 13 wherein an alcohol represented by the empirical formula $$R^1OH,$$

generated in the reaction of 2,4-pentanedione and the titanate represented by the empirical formula $(R^1O)_4Ti$, is removed prior to the introduction of at least one alcohol represented by the empirical formula $$R^3OH.$$

18. The process of claim 13 wherein the alcohol represented by the empirical formula $$R^1OH$$

has a lower boiling point than the alcohol represented by the empirical formula $$R^3OH$$

and the alcohol represented by the empirical formula $$R^1OH$$

is removed after completion of the reaction of said pentanedione, said titanate and said alcohol represented by the empirical formula $$R^3OH.$$

* * * * *